US009839578B2

(12) United States Patent
Thoresen et al.

(10) Patent No.: US 9,839,578 B2
(45) Date of Patent: Dec. 12, 2017

(54) NON-INVASIVE METHODS FOR PREVENTION, DETECTION, TREATMENT, AND HEALING OF NEOPLASTIC PROCESSES IN DOGS AND CATS

(71) Applicant: GOOD-IP LIMITED, Nicosia (CY)

(72) Inventors: Are Thoresen, Sandefjord (NO); Michael Schlosser, Haifa (IL)

(73) Assignee: GOOD-IP LIMITED, Nicosia (CY)

( * ) Notice: Subject to any disclaimer, the term of this patent is extended or adjusted under 35 U.S.C. 154(b) by 998 days.

(21) Appl. No.: 14/159,503

(22) Filed: Jan. 21, 2014

(65) Prior Publication Data
US 2015/0202119 A1    Jul. 23, 2015

(51) Int. Cl.
*A61B 17/34*        (2006.01)
*A61H 39/08*        (2006.01)
(Continued)

(52) U.S. Cl.
CPC ......... *A61H 39/086* (2013.01); *A61H 39/002* (2013.01); *A61H 39/04* (2013.01);
(Continued)

(58) Field of Classification Search
CPC ...... A61H 2201/1635; A61H 2201/164; A61H 2203/03; A61H 2205/065; A61H 2205/12;
(Continued)

(56) References Cited

U.S. PATENT DOCUMENTS 4,479,495 A    10/1984  Isaacson
5,676,684 A *  10/1997  Choi ..................... A61H 39/08
                                                       128/907
(Continued)

FOREIGN PATENT DOCUMENTS

CN        102716553 A    10/2012

OTHER PUBLICATIONS

Jong-Ho Jeong, Simple Acupoints Prescription Flow Chart Based on Meridian Theory: A Retrospective Study in 102 Dogs, Feb. 8, 2013.*

(Continued)

*Primary Examiner* — Jonathan Miles
*Assistant Examiner* — Majid Jamialahmadi
(74) *Attorney, Agent, or Firm* — Roach Brown McCarthy & Gruber, P.C.; Kevin D. McCarthy

(57) ABSTRACT

The invention is a method consisting of stimulation of specific new acupuncture points to prevent, treat and heal specific types of neoplastic process in dogs and cats. The specific acupuncture points used in the method of the invention have not been previously disclosed for the treatment of neoplastic processes. The treatments can be carried out by accredited practitioners in a clinical setting or by a layperson. The stimulation can be provided by any of the known techniques used for stimulation of controlling points, including, but not limited to, traditional acupuncture needles, auto-injector needles, electric acupuncture, acupressure, lasers, acupuncture lasers, UV radiation, infra-red radiation, heat, magnets, moxibustion, and a combination of two or more of these techniques, for example, the use of both needles and laser acupuncture simultaneously in a single treatment session.

12 Claims, 6 Drawing Sheets

(51) Int. Cl.
*A61H 39/00* (2006.01)
*A61H 39/04* (2006.01)
*A61H 39/06* (2006.01)
*A61M 5/52* (2006.01)
*A61N 2/00* (2006.01)
*A61N 5/06* (2006.01)
*A61N 2/06* (2006.01)
*A61N 5/067* (2006.01)

(52) U.S. Cl.
CPC ............... *A61H 39/06* (2013.01); *A61M 5/52* (2013.01); *A61N 2/006* (2013.01); *A61N 5/0619* (2013.01); *A61H 2039/005* (2013.01); *A61H 2201/10* (2013.01); *A61H 2201/164* (2013.01); *A61H 2201/1635* (2013.01); *A61H 2201/1666* (2013.01); *A61H 2201/1671* (2013.01); *A61H 2203/03* (2013.01); *A61H 2205/065* (2013.01); *A61H 2205/12* (2013.01); *A61N 2/06* (2013.01); *A61N 2005/067* (2013.01)

(58) Field of Classification Search
CPC .............. A61H 2205/125; A61H 39/04; A61H 39/086; A61H 39/08; A61N 5/0619; A61N 5/0622; A61N 5/067
USPC .................................................. 606/189, 204
See application file for complete search history.

(56) References Cited

U.S. PATENT DOCUMENTS

| | | |
|---|---|---|
| 6,306,160 B1 | 10/2001 | Nidetzky |
| 7,179,278 B2 | 2/2007 | Schikora |
| 2004/0000076 A1 | 1/2004 | Celmo |
| 2007/0129713 A1 | 6/2007 | Weber |
| 2013/0172969 A1* | 7/2013 | You .......................... A61F 7/034 607/114 |

OTHER PUBLICATIONS

Tsai-Ju Chien, Integrating Acupuncture Into Cancer Care, 2013.*
Thoresen et al., Acupuncture treatment on dogs with confirmed mammary cancer; observed tumor-regression and derivation of 12 cytostatic bioactive peptides applied with success on cancer cell in vitro, May 17, 2010.
Jeong et al., Simple accupoints prescription flow chart based on meridian theory: a retrospective study in 102 dogs. Evidence-based complementary and alternative medicine, vol. 2013, Article ID 129315, Apr. 9, 2013, pp. 1-13.
Are Simeon Thoresen DVM, "Holistic Veterinary Medicine", CreateSpace Independent Publishing Platform, North Charleston, South Carolina, USA 2nd Ed.,466-484 (2012).
International Search Report for PCT/IL2015/050066, dated Jun. 26, 2015, 2 pages.

* cited by examiner

NON-INVASIVE METHODS FOR PREVENTION, DETECTION, TREATMENT, AND HEALING OF NEOPLASTIC PROCESSES IN DOGS AND CATS

FIELD OF THE INVENTION

The invention is from the field of integrative veterinary medicine. Specifically the invention is from the field of stimulation of acupoints. More specifically the invention is from the field of acupuncture therapy and the stimulation of acupoints applied to the prevention, and treatment of a variety of types of neoplastic processes in dogs and cats.

BACKGROUND OF THE INVENTION

Acupuncture is one or of the oldest methods of treating disease having been used by the Chinese for over 4000 years. Without going into the philosophy behind it, the traditional Chinese method (TCM) is based on stimulating specific points on the body known as acupuncture points by penetrating the skin with thin sharp needles and manipulating the needles. The acupuncture points are located on paths called meridians through which energy flows throughout the body. Also a long standing aspect of TCM is a therapy called moxibustion, which involves burning a herb either directly on the patient's skin at an acupuncture point or in association with a needle.

Over the millennia that have passed since the origins of the practice of acupuncture new systems have evolved that use acupuncture points and meridians not recognized in the traditional Chinese method (TCM). Additionally new methods of applying the therapy that are non-invasive and do not require the use of needles have been devised. These methods include, for example, electric acupuncture, acupressure, and laser acupuncture.

Soft Lasers—low-intensity non-thermal laser irradiation treatments are used to stimulate traditional acupuncture points instead of needles; in other cases they are used to stimulate the traditional acupuncture points by applying the technique of moxibustion. Many different apparatuses have been described in the patent and non-patent literature for use in laser acupuncture. Some examples are:

U.S. Pat. No. 6,306,160 describes a hand held device that comprises an electrode used to locate acupuncture points by measuring skin resistance and a 3 mw diode laser that emits light with a wavelength of 635-670 nm.

U.S. Pat. No. 7,179,278 describes an apparatus in which one or more remote laser sources that emit light at 350-980 nm are optically linked by fiber optics to a handpiece that is in contact with the skin of the patient. The handpiece comprises two electrodes to measure skin resistance. The penetration depth is adjusted by changing the wavelength and also by reducing the diameter of the optical fiber as it approaches the tip of the handpiece.

US 2007/0129713 describes a laser needle for performing combined laser therapy and electric therapy. The output beam from a remote diode laser is conducted to the patient by an optical fiber. At its distal end the optical fiber is surrounded by a metal jacket having a disk attached to its lower end. The disk serves to distribute the electric current of the electric acupuncture over a larger area and also to aid in attaching the laser needle to the body of the patient.

CN102716553 is an example of a publication that describes an apparatus comprising two lasers that provides the combined effects of needle and moxibustion. The first laser is a red laser (635 nm) to simulate the effect of the needles and the second laser produces an output in the range of 1250-10000 nm to simulate the effect of thermal moxibustion.

Although there are innumerable reports of successful treatment of essentially every known condition relating to the physical and mental health of humans and animals, a considerable amount of controversy surrounding the efficacy of the method exists. This is in a large part due to the difficulty of devising and carrying out controlled clinical studies.

Are Thoresen, one of the inventors (henceforth "the first inventor") of the present invention, has been actively practicing acupuncture therapy since 1977. He has treated more than 600 patients—animals and humans—with various kinds of cancer, applying different methods. Some of the experience that he has accumulated over the years is summarized in a book that he has written in his native Norwegian. A $2_{nd}$ English edition has been published (Are Simeon Thoresen DVM, "Holistic Veterinary Medicine", CreateSpace Independent Publishing Platform, North Charleston, S.C., USA).

It is a purpose of the present invention to build on the first inventor's experience and his previous success by providing a system and method that is based upon the use of acupuncture points that have not previously been reported for prevention, and treatment of cancer in animals.

Further purposes and advantages of this invention will appear as the description proceeds.

SUMMARY OF THE INVENTION

In a first aspect the invention is a method for treating, by stimulation of specific acupoints, neoplastic processes that have previously been diagnosed in an organ in a dog or in a cat that is or is not currently undergoing other treatment. The method comprises the steps of:
  a) generating a therapy protocol comprising the specific acupoints to be stimulated;
  b) treating the dog or cat in a series of treatment sessions comprised of stimulation of the specific acupoints, which are located on its paws, wherein the stimulation can be provided by at least one of any stimulation means used to apply acupuncture therapy;
  c) applying known methods to evaluate the effect of the treatment on the neoplastic process,
  d) adjusting the therapy protocol according to the evaluation of the progress;
  e) repeating steps (b) to (d) until the treatment is deemed successful.

In embodiments of the treatment method of the invention:
  i) in step (a) an individual consults instructional material available to her/him and decides which of the specific acupoints should be stimulated and prepares a therapy protocol accordingly, without the assistance of a veterinarian or an accredited acupuncture practitioner;
  ii) in step (b) the treatment sessions are carried out by the owner of the dog or the cat or by another layperson;
  iii) in step (d) an individual, who can be the same or different from the individual of step (i) adjusts the treatment protocol with or without the help of a veterinarian or an accredited acupuncture practitioner.

In embodiments of the treatment method of the invention the at least one stimulation means is selected from the group including, but not limited to: traditional acupuncture needles, auto-injector needles, electric acupuncture apparatus, acupressure devices, lasers, UV radiation sources, infrared radiation sources, heat sources, magnets, fire, and a combination of at least two of these means.

In embodiments of the treatment method of the invention the treatment sessions are initially carried out once a week for at least 3 months.

In embodiments of the treatment method of the invention each treatment session comprises one of the following: using low-level laser radiation alone for 5 minutes for each relevant acupoint; using acupuncture needles alone for 10 minutes per acupoint; and using a combined treatment with acupuncture needles and low-level laser radiation comprised of using the acupuncture needles alone for 5 minutes followed by use of the low-level laser and the acupuncture needles together for an additional 5 minutes.

In embodiments of the treatment method of the invention the location of the acupuncture points on the paws of the dogs and the cats that are relevant for treatment of neoplastic processes occurring in specific organs are the acupoints A1 to A13 and B1 to B9.

In embodiments of the treatment method of the invention, a neoplastic process occurring in one of the following specific organs is treated by stimulating at least one acupuncture point associated with the organ, the associated acupoints located at the following locations:
  i. anus—A13=14/20 on the medial side of 5th metatarsal and B9=14/20 on the medial side of 5th metacarpal;
  ii. bladder—A2=11/20 on the medial side of 2nd metatarsal and B7=11/20 on the medial side of 5th metacarpal;
  iii. breast—A3=6/20 on the lateral side of 2nd metatarsal;
  iv. cervix—B3=between the distal 2/3 and the proximal 1/3 on the lateral side of the proximal digital bone of the 4th digit;
  v. kidney—A1 =10/20 on the medial side of 2nd metatarsal and B6=10/20 on the medial side of 5th metacarpal;
  vi. large intestine—A12=12/20 on the medial side of 5th metatarsal and B8=12/20 on the medial side of 5th metacarpal;
  vii. liver—B1=10/20 on the medial side of 1st metacarpal;
  viii. lungs—B5=6/20 on the medial side of 5th metacarpal;
  ix. ovary—A10=10/20 on the medial side of 5th metatarsal;
  x. pancreas—A5=9/20 on the lateral side of 2nd metatarsal;
  xi. prostata—A6=10/20 on the lateral side of 2nd metatarsal and A11=11/20 on the medial side of 5th metatarsal and B4=11/20 on the lateral side of 4th metacarpal;
  xii. rectum—A13=14/20 on the medial side of 5th metatarsal and B9=14/20 on the medial side of 5th metacarpal;
  xiii. small intestine—A8=8/20 on the medial side of 5th metatarsal;
  xiv. stomach—A4=8/20 on the lateral side of 2nd metatarsal;
  xv. testis—B2=11/20 on the medial side of 1st metacarpal;
  xvi. thyroid—A7=4/20 on the medial side of 5th metatarsal; and
  xvii. uterus—A6=10/20 on the lateral side of 2nd metatarsal and A9=10/20 on the medial side of 5th metatarsal and B4=11/20 on the lateral side of 4th metacarpal;
wherein, the locations are expressed as the lengths of the bones, which are divided into twenty parts starting from the distal end and each of the acupoints is located within the indicated 20th part of the bone.

In embodiments of the treatment method of the invention the corresponding points on both front paws or on both rear paws are stimulated either simultaneously or consecutively.

In embodiments of the treatment method of the invention, after the treatment is deemed successful, treatment sessions are carried out periodically for the remainder of the animal's life.

In a second aspect, the invention is a method for preventing the occurrence of a specific type of neoplastic process in any given dog or cat, including a dog or cat having a family history or genetic makeup that increases its risk of contracting the specific type of neoplastic process. The preventive method comprises periodically carrying out a preventive treatment session comprised of stimulation of the specific acupuncture points A1 to A13 and B1 to B9 that are relative to the specific type of neoplastic process.

In embodiments of the prevention method of the invention each preventive treatment session comprises one of the following: using low-level laser radiation alone for 5 minutes for each relevant acupoint; using acupuncture needles alone for 10 minutes per acupoint; and using a combined treatment with acupuncture needles and low-level laser radiation comprised of using the acupuncture needles alone for 5 minutes followed by use of the low-level laser and the acupuncture needles together for an additional 5 minutes.

In embodiments of the prevention method of the invention the preventive treatment sessions are carried out once every three months.

In embodiments of the treatment method of the invention the treatment session is carried out with the aid of at least one of:
  a. personalized gloves that comprise holes directly over the specific acupoints that should be stimulated for the specific type of neoplastic process; and
  b. an apparatus that is adapted to position and to support the stimulation means above the specific acupoint that should be stimulated for the specific type of neoplastic process at the correct location and angle.

In embodiments of the prevention method of the invention the preventive treatment session is carried out with the aid of at least one of:
  a. personalized gloves that comprise holes directly over the specific acupoints that should be stimulated for the specific type of neoplastic process; and
  b. an apparatus that is adapted to position and to support the stimulation means above the specific acupoint that should be stimulated for the specific type of neoplastic process at the correct location and angle.

In a third aspect the invention is a kit comprising instructions for preventing and treating neoplastic processes by stimulation of specific acupoints. The kit may comprise at least one of:
  a. stimulating means for carrying out the treatment; and
  b. an apparatus for locating stimulating means on the specific acupoints.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

Figure 1:
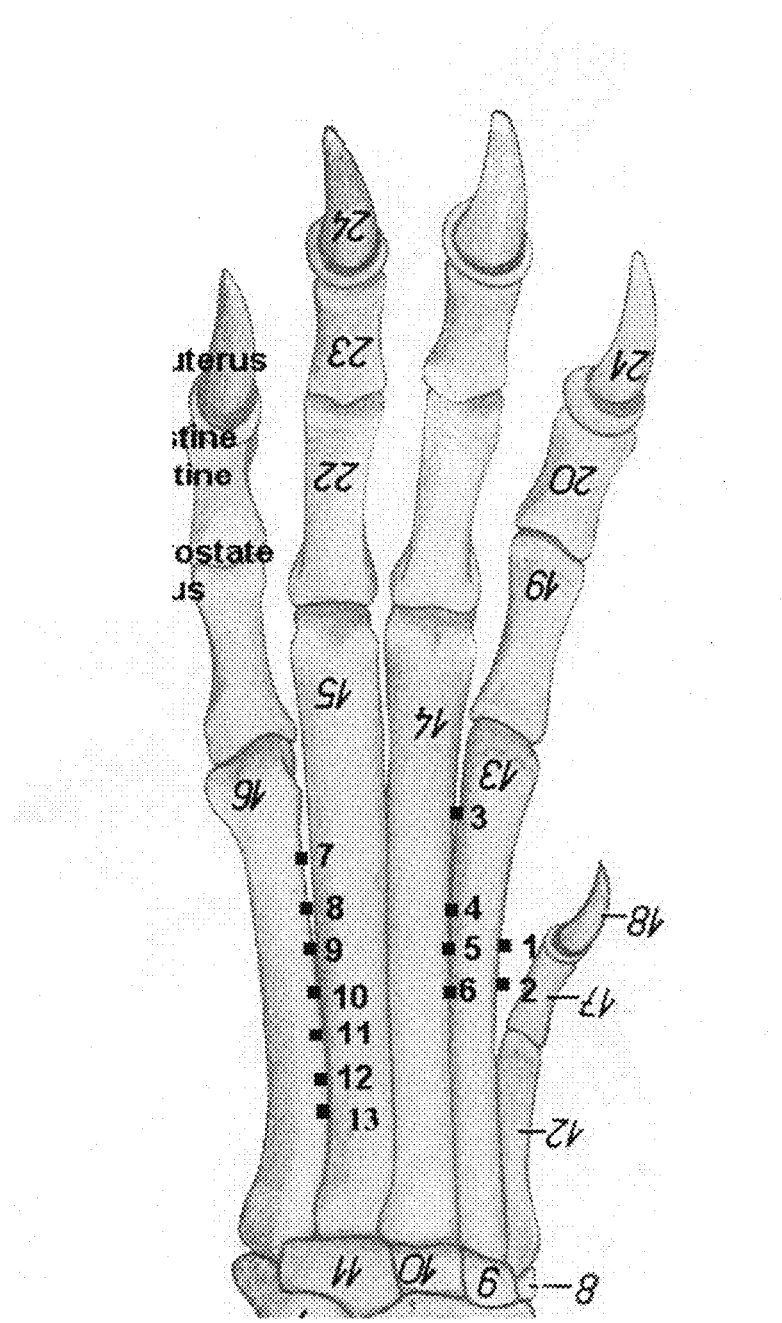
FIG. 1 and FIG. 2 respectively show the locations of the new acupuncture points of the invention on the bones of a left hind paw (foot) of a dog, and a left front paw (hand) of a dog.

The invention is a method consisting of stimulation of specific acupuncture points to prevent, and treat specific types of neoplastic processes, herein referred to for simplicity as cancer, that occur in dogs and cats, frequently referred to herein as animals. Although the acupoints and treatment methods of the invention will be mostly applied to pet and working dogs and to household cats they are applicable to all members of the feline and canine families. Herein the term "neoplastic process" refers to the formation and growth of an abnormal growth of tissue in animals. The abnormal growth can be benign or malignant and is herein sometimes referred to as a cancer or a tumor. In many cases treatment according to the methods of the invention may lead to complete healing of the neoplastic process.

The specific acupuncture points used in the method of the invention have not been previously disclosed as effective for the treatment of cancer. The treatments can be carried out by accredited practitioners in a clinical setting or by the animal's owner or other layperson at any convenient location. When the treatments are carried out by the owner or a layperson, they can be guided by instructions from an accredited practitioner or by instructional material, e.g. instruction manuals, video recordings, and applications on mobile devices. The stimulation can be provided by any of the known techniques used for stimulation of controlling acupoints, including, but not limited to, traditional acupuncture needles, electric acupuncture, acupressure, laser, acupuncture laser, UV radiation, infra-red radiation, heat, fire, magnets, moxibustion, and a combination of two or more of these techniques. For example, the use of both needles and laser acupuncture simultaneously in a single treatment session or two lasers aimed at the same acupoint from different angles. In addition to the use of conventional acupuncture needles the inventors also envisage that an acupuncture needle supplied as an auto-injector similar to those used to inject insulin would be a very useful aid to many non-professionals. Herein the generic term "stimulation techniques" refers to all of these techniques, but not limited to them, collectively. Herein the generic term "stimulation means" collectively refers to the devices or means, e.g. conventional needles, auto-injector needles, electric acupuncture apparatus, acupressure devices, lasers, UV radiation sources, infra-red radiation sources, heat sources, magnets, fire, and a combination of at least two of these means used to apply the stimulation techniques.

Equipment that can be useful in carrying out the method of the invention includes a laser device specifically designed for applying laser radiation to acupuncture points and apparatus including articles of clothing and an apparatus adapted to serve as guides to accurately locate the acupuncture points and apply the treatment.

The present invention differs from the earlier work described in the above referenced book authored by the first inventor in three ways: firstly new acupoints have been discovered for treatment of various types of cancer and secondly, in addition to acupuncture needles, other types of stimulation devices or combination of some of them are used to stimulate the acupoints and new acupuncture protocols have been developed. Thirdly, the method of the invention is adapted to be used for preventing cancer as well as treating it—which has not been done using acupuncture techniques previously.

The first inventor has identified acupuncture points that are effective for stimulating the bodies of dogs and cats for treatment of 16 different types of cancer. The use of these acupuncture points in the treatment of cancer has never been reported before.

The types of cancer that can be treated using the new acupuncture points are: kidney, bladder, breast, stomach, pancreas, prostate, uterus, thyroid, small intestine, large intestine, ovary, rectal-anus, liver, testis, cervix, and lung.

Figure 2:
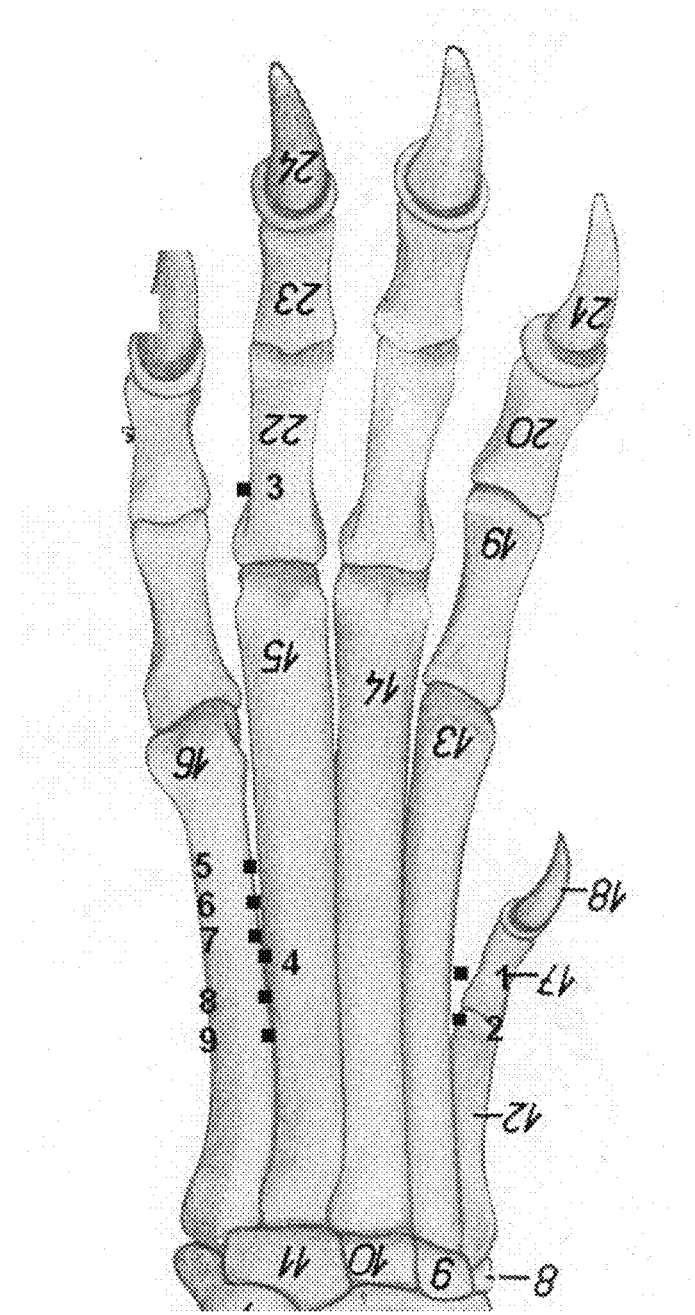

FIG. 1 and FIG. 2 respectively show the locations of the acupuncture points of the invention on the bones of a left hind paw (foot) of a dog, and a left front paw (hand) of a dog. In each of these figures a small black square represents the location of the acupoint and a number next to the square identifies the type of cancer that is treated by the respective acupuncture point. The acupoints numbered 1-13 in FIG. 1 will also be referred to herein as A1 to A13 respectively and the acupoints numbered 1-9 in FIG. 2 will also be referred to herein as B1 to B9 respectively.

All of the points are located close to the bones, as shown in the drawings. To indicate the locations of the points on the bones, the bone is divided into 20 parts, starting from the distal end (closest to the end of the finger or toe), and ending at the proximal end. The point is located then within a 1/20-part of the length of the bone, as listed in the following tables, wherein Table 1, relates to FIG. 1 and Table 2 to FIG. 2 and the first column in each table contains the numbers that identify the acupoints in the respective figure.

TABLE 1

Dog Hind Paw (FIG. 1)

| NUMBER | ORGAN | BONE | LOCATION |
|---|---|---|---|
| 1 = A1 | Kidney | $2^{nd}$ metatarsal | 10/20 |
| 2 = A2 | Bladder | $2^{nd}$ metatarsal | 11/20 |
| 3 = A3 | Breast | $2^{nd}$ metatarsal | 6/20 |
| 4 = A4 | Stomach | $2^{nd}$ metatarsal | 8/20 |
| 5 = A5 | Pancreas | $2^{nd}$ metatarsal | 9/20 |
| 6 = A6 | Prostata & Uterus | $2^{nd}$ metatarsal | 10/20 |
| 7 = A7 | Thyroid | $5^{th}$ metatarsal | 4/20 |
| 8 = A8 | Small Intestine | $5^{th}$ metatarsal | 8/20 |
| 9 = A9 | Uterus | $5^{th}$ metatarsal | 10/20 |
| 10 = A10 | Ovary | $5^{th}$ metatarsal | 10/20 |
| 11 = A11 | Prostate | $5^{th}$ metatarsal | 11/20 |
| 12 = A12 | Large Intestine | $5^{th}$ metatarsal | 12/20 |
| 13 = A13 | Rectum & Anus | $5^{th}$ metatarsal | 14/20 |

TABLE 2

Dog Front Paw (FIG. 2)

| NUMBER | ORGAN | BONE | LOCATION |
|---|---|---|---|
| 1 = B1 | Liver | $1^{st}$ metacarpal | 10/20 |
| 2 = B2 | Testis | $1^{st}$ metacarpal | 11/20 |
| 3 = B3 | Cervix | the proximal digital bone | between the distal 2/3 and the proximal 1/3 |
| 4 = B4 | Prostata & Uterus | $4^{th}$ metacarpal | 11/20 |
| 5 = B5 | Lungs | $5^{th}$ metacarpal | 6/20 |
| 6 = B6 | Kidney | $5^{th}$ metacarpal | 10/20 |

TABLE 2-continued

Dog Front Paw (FIG. 2)

| NUMBER | ORGAN | BONE | LOCATION |
|---|---|---|---|
| 7 = B7 | Bladder | $5^{th}$ metacarpal | 11/20 |
| 8 = B8 | Large Intestine | $5^{th}$ metacarpal | 12/20 |
| 9 = B9 | Rectum & Anus | $5^{th}$ metacarpal | 14/20 |

All of the acupoints shown in the figures and listed in Tables 1 and 2 have corresponding points on both front paws or on both rear paws. For example, cancer of the liver in a dog can be treated by stimulating acupoint B1 at the midpoint (10/20) of the medial side of the $2^{nd}$ metacarpal bone on the right front paw as shown in FIG. 2 and an acupoint at the midpoint (10/20) on the medial side of the $2^{nd}$ metacarpal bone on the left front paw. In addition self-healing of some types of cancers, e.g. kidney, will be stimulated by stimulating acupoints on both the front paw and the rear paw. In all of these cases the recommended treatment protocol calls for stimulating all of the relevant points on both left and right paws, either simultaneously or consecutively.

According to the present invention, in addition to the use of needles, the accupoints can be stimulated by any known stimulation techniques. In particular the present invention proposes the use of low-level laser (also known as soft laser) radiation or a combination of needles and low-level laser radiation as will be described herein below.

Most devices used in laser acupuncture produce an output beam having a small footprint on the skin (typically a round footprint with a diameter of approximately 1 mm and an area of approximately 0.8 $mm^2$). One of the reasons that acupuncture treatments can only be administered by registered practitioners is the long learning curve need to learn how to locate the acupoints and accurately insert the needle. With needles the success of the treatment depends on accuracy of placement of the needles and the angle at which the needle is inserted, which in some cases is not perpendicular to the skin surface. With narrow output beam lasers similar conditions must be satisfied for successful treatment.

The inventors have conceived of the idea of using a laser apparatus that produces a long and narrow beam of laser light, which can be aligned with the bone and centered approximately at the location of the acupoint in order to overcome the problems associated with the level of exactness required when using needles or small diameter laser beams and to make it possible for non-professionals, including the patient her/himself, to administer the treatment following a recommended protocol. The laser device produces a fully coherent output beam (having an energy density that is uniform in magnitude over the entire rectangular, elliptical, or circular footprint, which in a non-limiting, illustrative embodiment can be approximately 450 $mm^2$. Using a laser device that produces an output beam having a large footprint on the skin that is powerful enough to stimulate the acupoint means that the center of the laser beam does not have to be located exactly over the acupoint.

The apparatus for producing the laser beam is similar to a commercially available apparatus that is manufactured and sold by the applicant of the present invention under the name B-CURE™ laser. This apparatus was designed and is being used to apply laser light for a wide variety of therapeutic purposes. The B-CURE™ laser is a light weight hand-held device that can be used by both health care professionals and non-professionals, including the owners of dogs and cats in their homes. The apparatus is described in patent applications that have been filed and published in several countries, e.g. US2011/0032960.

In order to see if the use of a large footprint laser beam as proposed in this invention could effectively produce similar results to those achieved using acupuncture needles a pilot investigation was carried out by the first inventor. The procedure consisted of stimulation of an area situated between Os metatarsale II and III in 14 dogs having mammary cancer and 6 dogs having mammary tumors. The stimulation of the area mentioned was done with direct and close laser radiation by a 250 mW B-CURE™ laser held against the area for 4 minutes, once a month for a total of 4 times.

The following table presents a summary of the results of treating mammary cancer in twenty dogs with a B-cure laser. The cases described represent a consecutive case series of treatment of dogs with mammary cancer. They were not selected to show the best outcomes. The development of the tumors was followed up for several months.

TABLE 3

Summary of the Results of Treating Mammary Cancer and tumours with a "B-Cure Laser" soft Laser device

| # | Cancer type/description of tumour/malignancy and indication of malignant (M) or benign (B) | Patient/year of birth/Number of treatments | Results (positive effect (P), uncertain (?) or no effect (N)) |
|---|---|---|---|
| 1 | Mammacarcinoma/ 10 & 8 mm. tumors in both sides/(M) | Female dog, English setter/2009/3 | The tumors went almost totally away after 8 weeks, then reappeared 4 weeks later, and reached the size of ca 2-3 mm, and are now stable after 4 months. No other treatment (P) |
| 2 | Mammacarcinoma/ 65 mm. tumor left side/(M) | Female dog, Mastiff/ 2008/3 | The tumor did totally disappear after 6 weeks, and only a small lump of connective tissue of 3 mm remains. No other treatment (P) |
| 3 | Mammacarcinoma/6 tumors right side, differing between 3 and 11 mm/(M) | Female Dog, mixed breed/2006/3 | The tumors were totally gone after 11 weeks. No other treatment (P) |

TABLE 3-continued

Summary of the Results of Treating Mammary Cancer and tumours with a "B-Cure Laser" soft Laser device

| # | Cancer type/description of tumour/malignancy and indication of malignant (M) or benign (B) | Patient/year of birth/Number of treatments | Results (positive effect (P), uncertain (?) or no effect (N)) |
|---|---|---|---|
| 4 | Mammacarcinoma/ 45 mm tumor left side/ (M) | Female dog, Riesenschnauser/ 2004/4 | The tumor shrank to 15 mm after 4 months. No other treatment (P) |
| 5 | Mammacarcinoma/ 94 mm tumor right side/(M) | Female dog, mixed breed/2009/3 | The tumor was reduced by 60% after 4 months. No other treatment. (P) |
| 6 | 1 Mammary tumour: diameter 1.1 cm/(B) | Female dog, English setter/2007/3 | The tumor is at the same size as when the treatment started 4 months ago. No other treatment. (?) |
| 7 | 2 Mammary tumours: diameter 14 mm and 11 mm right side/(B) | Female dog, English setter/2007/4 | The tumors are reduced by 15% after 4 months. No other treatment. (P?) |
| 8 | Mammacarcinoma/ 10 & 23 mm. tumors in both sides/(M) | Female dog, Riesenschnauser/ 2005/3 | The tumors continued to grow, but at a reduced rate. After 4 months the same results. No other treatment. (N) |
| 9 | Mammacarcinoma/ 85 mm. tumor right side/(M) | Female dog, Golden retriever/2008/4 | The tumor is reduced with 80% after 3, 5 months. No other treatment. (P) |
| 10 | 1 Mammary tumour: diameter 16 mm/(B) | Female dog, Mixed breed/2009/3 | The tumor was reduced to 3 mm after 3, 5 months. No other treatment. ( P ) |
| 11 | Mammacarcinoma/ 28 mm. tumors left side/(M) | Female dog, Buhund Norwegian/2006/3 | The tumor almost went totally away after 4 weeks, then reappeared 2 weeks later, and reached the size of ca 2-3 mm, and is now stable after 3 months. No other treatment (P) |
| 12 | Mammacarcinoma/ 55 mm. tumor left side/malign (M) | Female dog, Richback/2005/3 | The tumor totally disappeared after 6 weeks, and only a small lump of connective tissue of 3 mm remains. No other treatment (P) |
| 13 | Mammacarcinoma/4 tumors left side, 13, 18, 20 and 25 mm/ (M) | Female Dog, mixed breed/2006/3 | The tumors were totally gone after 10 weeks. No other treatment (P) |
| 14 | Mammacarcinoma/ 45 mm tumor left side/ (M) | Female dog, Grand Danois/2004/3 | The tumor has shrunk to 15 mm after 3 months. No other treatment (P ) |
| 15 | Mammacarcinoma/ 114 mm tumor left side/(M) | Female dog, mixed breed/2009/3 | The tumor was reduced to 34 mm after the 3 months. No other treatment. (P) |
| 16 | 1 Mammary tumour: diameter 30 mm right side/(B) | Female dog, Pekingnese/2005/3 | The tumor has grown to 35 mm in 3 months and 3 treatments. No other treatment. (?) |
| 17 | 3 Mammary tumours: diameter 14 mm and 21 mm and 34 mm, right side/(B) | Female dog, English setter/2008/3 | The tumors were reduced by 25% after 3 months. No other treatment. (P?) |
| 18 | Mammacarcinoma/ 30 & 43 mm. tumors in both sides/(M) | Female dog, Riesenschnauser/ 2006/3 | The tumors continued to grow for 2 months, but the last month there has been no growth. No other treatment. (N) |
| 19 | Mammacarcinoma/ 70 mm. tumor right side/(M) | Female dog, Golden retriever/2007/3 | The tumor is completely gone after 3 months. No other treatment. (P) |
| 20 | 1 Mammary tumour: diameter 15 mm/(B) | Female dog, Mixed breed/2009/3 | The tumor is reduced to 5 mm after 3 months. No other treatment. (P) |

The results here are similar to those that the first inventor has observed on >600 human and animal cancer patients in his own clinic using acupuncture needles to provide the stimulation to induce the self-healing. The overall results shown in table 3 are very promising. Of the 14 dogs with Mammacarsinoma there were 12 Positive results. Of the 6 dogs with Mammary Tumours there were 4 Positive results. In total 16 of the 20 dogs responded positively to the treatment. The positive effects were observed after 4 treatments over a total period of 4 months. These results provide a strong indication that stimulation of the specific acupoints using a large footprint laser beam will be effective.

As mentioned above, one of the reasons that acupuncture treatments are carried out only by licensed practitioners is the level of experience necessary to accurately locate the acupuncture point and to insert the needle or align the laser beam. The inventors propose to overcome these problems by providing the following aids at least one of which can be employed by the user to assist him/her to accurately locate and stimulate the required acupoints:

A stimulation source in the form of a hand held device that illuminates a rectangular, elliptical, or round area of the skin of the patient with light. An embodiment of the light emitting stimulation source is a laser device that emits infrared radiation and comprises a second light source that emits a visible light that overlaps or outlines the invisible beam emitted by the infrared laser diode;

Personalized gloves that comprise holes located directly over the acupoints that correspond to the points that should be stimulated for the specific type of cancer.

An apparatus that is adapted to fix the paw of the animal and to position and to support the stimulation means, e.g. laser device or needle, above the acupoint at the correct location and angle.

A video camera can be used to observe the relevant body part and produce images that, when used in conjunction with a processor and appropriate software and optionally with input from an experienced practitioner, can be displayed to the user to enable him/her to locate the desired acupoint and to insert the needle or aim the laser beam to that spot.

In embodiments of the invention the user and the licensed acupuncturist or veterinarian are at separate locations. Both possess devices, e.g. smartphones, tablets, or computers, comprising dedicated software and connected to a communication network, e.g. the internet or a cellular network, which allows them to share images taken by the video camera and other information and to communicate with each other. In these embodiments the practitioner can be actively involved in the home treatment session, for example by marking the location of the acupoint/s to be treated on the screen image of the patient.

Figure 3:
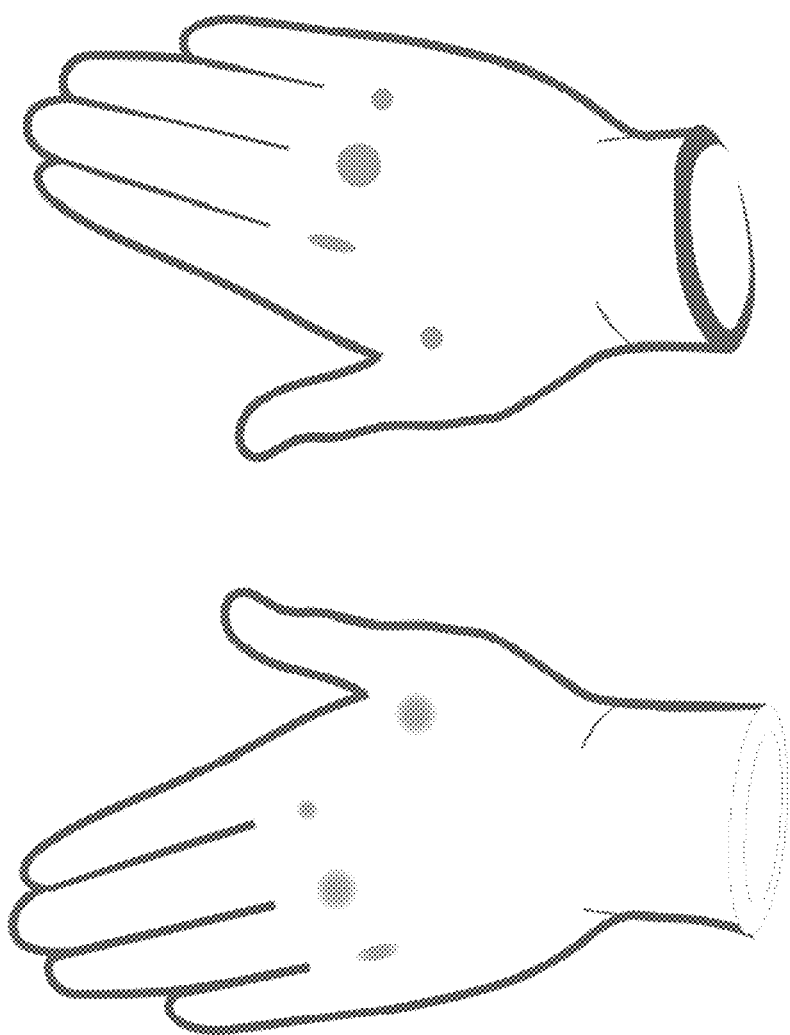
FIG. 3 schematically shows a glove adapted for use in the method of the invention.

FIG. 3 schematically shows a glove adapted for use in the method of the invention. The glove shown is for a human hand but similar gloves adapted mutatis mutandis can be provided in a number of sizes and in left and right hand versions to insure a correct fit to the paws of a cat or dog.

Unpersonalized gloves can be produced in a number of models, each with pre-cut holes at the known location of the acupoints for treatment of one or more types of disease or conditions. Embodiments of the unpersonalized gloves will be made available with the size, and the name of the disease/s the holes represent printed on them.

The glove shown in FIG. 3, or at least part of it, can be made from transparent material, to assist in locating the acupoint.

Alternatively, the attending veterinarian or accredited acupuncture practitioner that recommends and supervises the treatment can personalize the glove by creating holes at the location of the acupoints that are appropriate for the specific symptoms of his patient. In order to individualize the glove or sock such that the placement of the holes conforms to the exact anatomical structure and dimensions of the animal, in embodiments of the gloves at least a part of the glove is manufactured from transparent material. In the first session with the practitioner, the glove having the closest fit is placed on the paw of the animal and the practitioner locates the appropriate acupoint/s, marks the location/s on the glove, and makes holes of the required size. In one embodiment the practitioner, guided by FIGS. 1 and 2, locates the acupoints and marks them on the skin before the glove is put on the animal's paw. The marks on the skin can then be seen through the transparent material and transferred to the glove to mark the locations at which the holes should be created.

These holes in the glove will allow the animals owner to apply the stimulation treatment by him/herself, whether using traditional acupuncture needles, auto-injector needles, a prior art narrow beam laser device, the wide beam laser device described herein above, a combination of needles and the wide beam laser device simultaneously, or any other stimulation means.

Embodiments of the gloves comprise ridges around the holes or have a framework attached to them over the holes. The ridges or framework are adapted to help to hold the device used to apply the stimulation in a fixed position and orientation over the acupoint.

Figure 4:
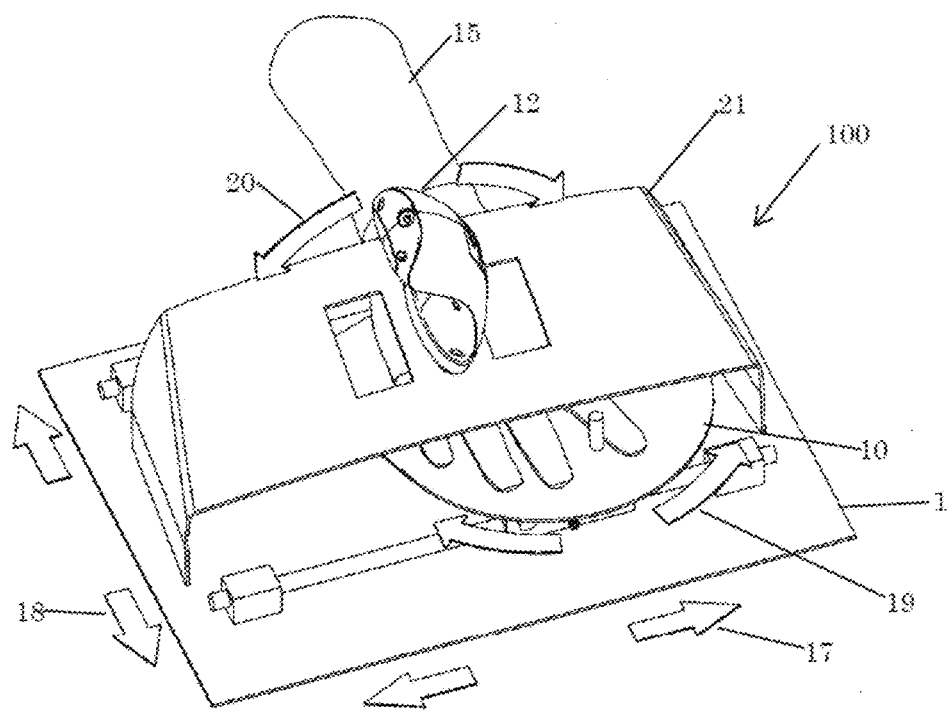
FIG. 4 to FIG. 6B schematically show an apparatus adapted to allow an inexperienced person to administer acupuncture treatment.
Figure 5:
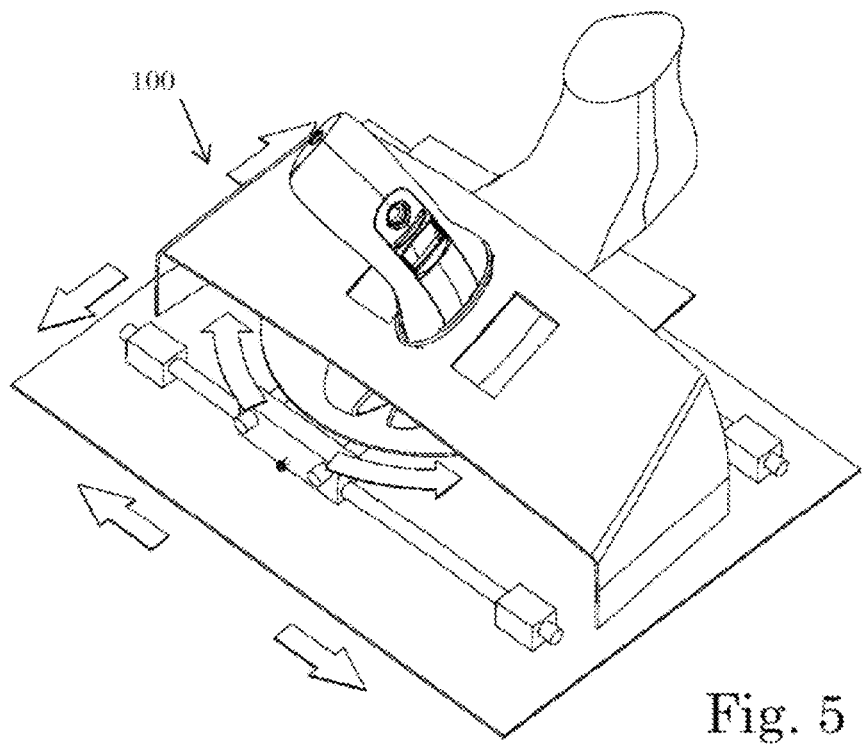

FIG. 4, FIG. 5, FIG. 6A, and FIG. 6B schematically show an apparatus adapted to allow an inexperienced person to administer acupuncture treatment. The apparatus shown in these figures is configured for use with humans but can be modified mutatis mutandis for use with dogs or cats as schematically shown in FIG. 7. The apparatus is designed to position the stimulation device at the correct location over the acupoint and at the correct angle and to support the device during the treatment period. FIG. 4 shows the apparatus adapted for use with a human hand. FIG. 5 shows the apparatus adapted for use with a human foot. The main features of apparatus 100 are identified in FIG. 4. Other components of apparatus 100 are described in more detail with respect to FIG. 6A and FIG. 6B.

The framework of apparatus 100 that supports all other components is comprised of a base plate 1 to which is rigidly attached a rigid bridge 21. Between the base plate 1 and bridge 21 is located a platform 10. Platform 10 is mounted in such a way that it has two linear degrees of freedom—back and forth and right and left motion in directions parallel to two perpendicular sides of base plate 1 (indicated by arrows 17 and arrows 18) and one rotational degree of freedom—clockwise and counterclockwise (indicated by arrows 19) around an axis perpendicular to base plate 1 that passes through the center of platform 10. In the center of the bridge is at least one opening through which the laser device 12 is placed so that it can irradiate the surface of platform 10. A framework 13 which supports laser device 12 is attached to the bridge at the edge of the opening by means of a hinge adapted to allow laser device 12 to be tilted (indicated by arrows 20) relative to the surface of bridge 21. The tilt of the laser device gives the apparatus a fourth degree of freedom, which is important because some of the acupoints are located on the side of a bone and have to be stimulated at an angle to the perpendicular to achieve a positive result from the treatment. The paw 15 being treated is placed on the platform 10 and optionally fixed in place with the aid of straps or other means.

The platform is then moved linearly and rotated until the location of the acupoint to be treated is under the center of the laser device 12. Platform 10 is now fixed in the correct position and at the correct orientation by locking its tilt angle and linear and rotational movements and the treatment can be started. In embodiments of the invention the locking mechanisms for the translational, rotational, and tilt motions comprise a series of marks that identifies the position at which each of the respective mechanisms is locked. After the initial location of the point at which the therapy should be applied is determined by the practitioner, the values of these marks are recorded and form a part of the treatment protocol for the animal, enabling the correct location for applying the therapy to be easily found in subsequent sessions.

Figure 6A:
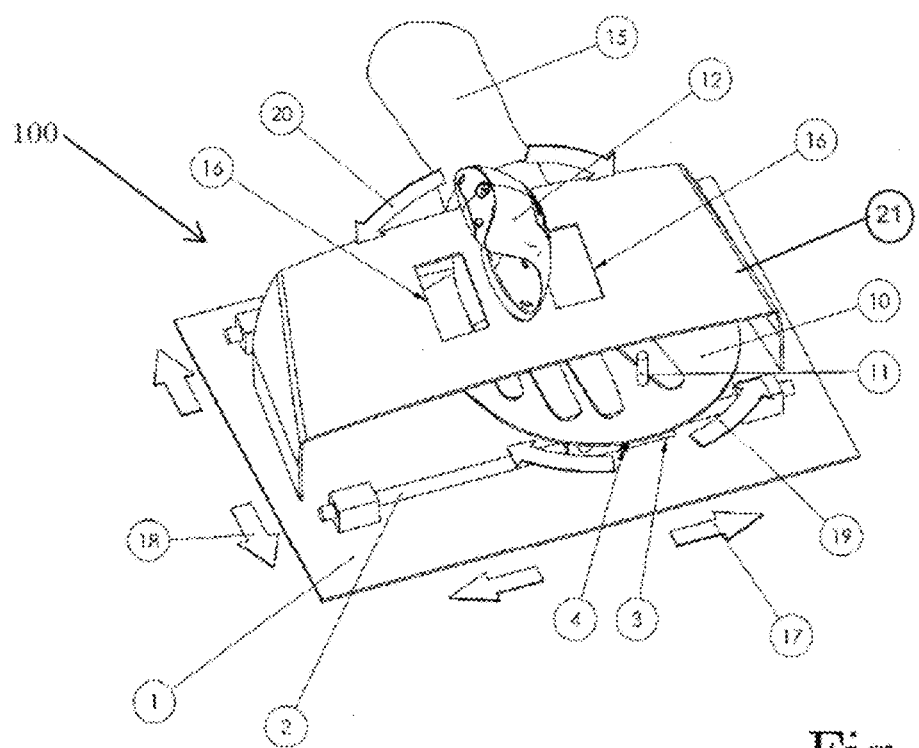
Figure 6B:
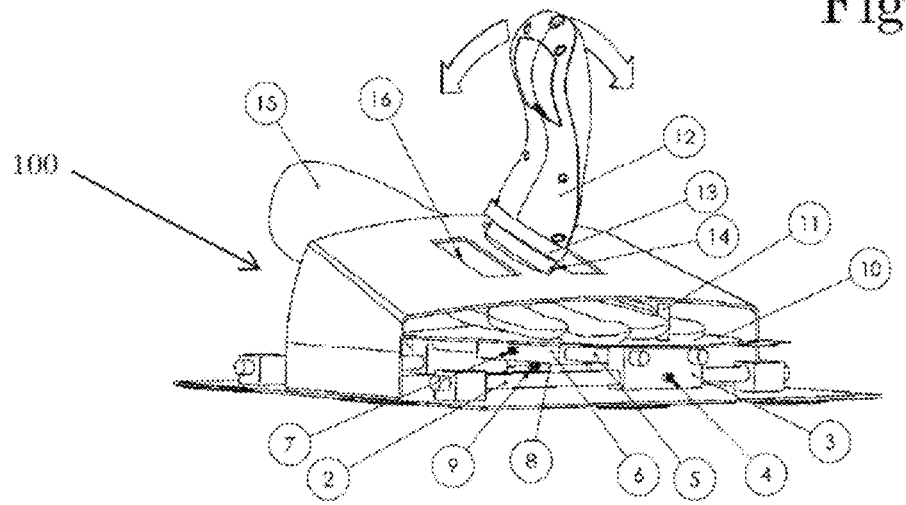
Figure 7:
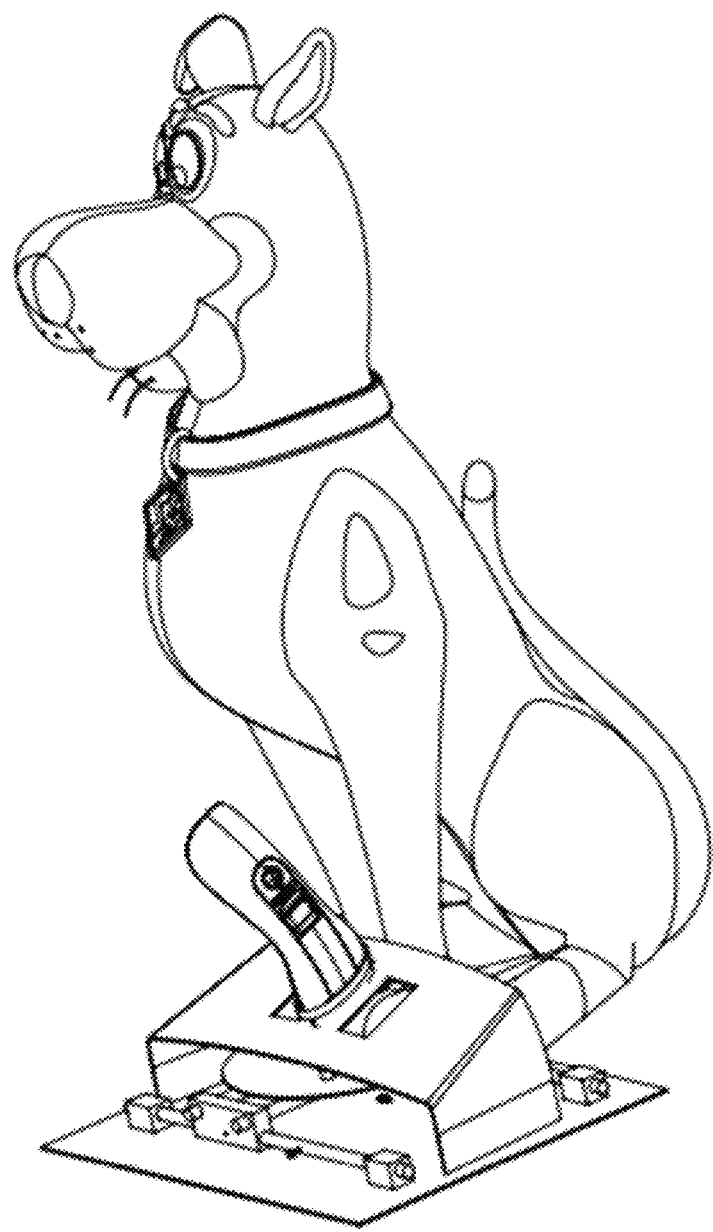
FIG. 7 schematically shows the apparatus of FIG. 4 to FIG. 6B adapted for use with a dog.

Referring to FIG. 6A and FIG. 6B other components of apparatus 100 are:

X-direction rail 2, two parallel rails 2 are attached on opposite sides of base plate 1;
X-direction carriage 3, one of which rides on each of rails 2;

X-direction carriage lock 4, which, when locked, prevents movement of carriage 3 along rail 2;

Y-direction rail 5, two parallel rails 5 are attached at their ends to the two carriages 3;

Y-direction carriage 6, one of which rides on both of rails 5;

Y-direction carriage lock 7, which, when locked, prevents movement of carriage 6 along rails 5;

Z-axis pivot 8, which is attached to carriage 6 and supports platform 10;

Z-axis lock 9, which, when locked, prevents rotation of platform 10;

Locating pins 11, used to position the organ 15 to be treated, e.g. hand, on platform 10 and to maintain that position during the alignment and treatment procedures;

Framework 13 of laser device 12;

Hinge 14 that connects framework 13 to bridge 21 of apparatus 100 (not shown in the figures is a lock to prevent tilt of laser device 12); and Windows 16 or openings in the top of bridge 21 that allow observation of the treatment area on the organ 15 being treated.

In the figures the apparatus 100 is adapted for use with a wide beam laser device but apparatus 100 can be modified mutatis mutandis for use with any of the stimulation means that is used to apply acupuncture treatment, e.g. conventional acupuncture needles or other types of laser devices.

Because apparatus 100 supports the stimulation and healing device during treatment, it is especially useful in a clinical environment where the use of several of these apparatuses will allow a single practitioner to simultaneously treat several acupoints on the same animal, e.g. the corresponding point on the right and left paw, or to treat several animals simultaneously. The use of more than one apparatus will eliminate the advantage that the use of needles has over lasers in treatment protocols that require stimulation of several acupoints on the same animal to be treated at once.

In embodiments of the invention a glove similar to that shown in FIG. 3, configured for use with the paw of a cat or dog, is used in conjunction with apparatus 100, configured for use with the paw of a cat or dog, in order to more easily locate the desired acupoint.

An embodiment of the method of the invention for treatment of a patient known to have a cancer affecting one of the organs listed herein above is carried out as follows:

The owner brings his/her dog or cat to his veterinarian or accredited acupuncture practitioner who identifies the acupoints to be stimulated and prepares a therapy protocol.

If the animal is being given medication for treatment of the disease, she/he is encouraged to continue with this during the course of the treatment according to the method of the invention.

Initially the treatment sessions will be carried out once a week for at least 3 months.

The duration of each treatment session depends on the type of stimulation that will be applied to the acupoints. Each treatment session with the laser apparatus will last for 5 minutes for each relevant acupoint. Treatment sessions using acupuncture needles will last 10 minutes per acupoint. For treatment sessions using a combination of needles and laser light, the needles alone will be used for the first 5 minutes followed by stimulation with both the laser and the needles for an additional 5 minutes.

The treatment sessions can be carried out by health care professionals in a hospital, clinic, or home environment; however, because of the relatively low cost and ease of operation of the laser apparatus, it is envisaged by the inventors that most of the sessions using the laser apparatus will be carried out by the animal's owner or another layperson in a non-clinical setting, e.g. the animal's home. Other scenarios are possible, e.g. one session per month carried out by an acupuncture practitioner followed by three home sessions with the laser apparatus or all self-treatments without the assistance of a professional. Where, and by whom, the stimulation will be administered will be determined on an individual basis taking into account factors such as the owner's ability to bring his animal to a clinic when required, the ability of the owner to carry out the sessions according to the schedule, and financial considerations.

The patient periodically visits his veterinarian or a specialist who uses known methods to evaluate the effect of the treatment on the tumour.

According to the progress the veterinarian, or accredited acupuncture practitioner adjusts the treatment protocol, e.g. the type of stimulation to be applied and duration and frequency of treatment sessions.

This cycle is repeated as long as necessary until the treatment is deemed successful. As a general rule it is anticipated that in most cases positive results will be seen in three months, therefore it is recommended anyway not to stop the treatment before the end of the third month. After successful treatment it is recommended to continue with the treatment at a clinic or at home for a much longer period of time, for example once every month for the first year, and once every two months for life.

Because using the laser acupuncture is easy to do at home, it is recommended that any dog or cat owner who wishes to do so and specifically owners whose animals are at high risk of contracting a specific type of cancer, as determined by family history or their genetic makeup, follow a protocol of laser radiation of the specific acupoint/s of this invention that is associated with that type of cancer as a preventive treatment. An example of a protocol of a preventive treatment is a session, as described herein above, once every three months.

It is noted that although the gloves and apparatus described herein above are useful aids to help both experienced professional practitioners and inexperienced persons to locate and stimulate the acupoints, their use is not a requirement of the method. The acupoints can also be stimulated by use of a hand-held wide-beam laser device or by the use of needles in the conventional way for prevention and treatment of cancer.

Although embodiments of the invention have been described by way of illustration, it will be understood that the invention may be carried out with many variations, modifications, and adaptations, without exceeding the scope of the claims.

The invention claimed is:

1. A method for treating, by stimulation of specific acupoints, neoplastic processes that have previously been diagnosed in an organ in a dog or in a cat that is or is not currently undergoing other treatment, said method comprising the steps of:

a) generating a therapy protocol comprising the specific acupoints to be stimulated;

b) treating said dog or cat in a series of treatment sessions comprised of stimulation of at least one of said specific acupoints that are associated with said organ in said dog or cat, which are located on its paws, wherein said stimulation can be provided by at least one of any stimulation means used to apply acupuncture therapy;

c) evaluating the effect of the treatment on the neoplastic process; and d) adjusting said therapy protocol according to said evaluation of the progress;

wherein, each said acupoint location is identified by a number ranging from 1 to 20 that corresponds with a location along a specific bone, each specific bone is divided into twenty parts starting from the distal bone end being the $1^{st}$ bone part and the proximal bone end being the $20^{th}$ bone part and wherein the specific acupoints that are associated with the following organs are:

i) anus—A13 is at the $14^{th}$ bone part on the medial side of 5th metatarsal and B9 is at the $14^{th}$ bone part on the medial side of 5th metacarpal;

ii) bladder—A2 is at the $11^{th}$ bone part on the medial side of 2nd metatarsal and B7 is at the $11^{th}$ bone part on the medial side of 5th metacarpal;

iii) breast—A3 is at the $6^{th}$ bone part on the lateral side of 2nd metatarsal;

iv) cervix—B3 is between the distal ⅔ and the proximal ⅓ on the lateral side of the proximal digital bone of the 4th digit;

v) kidney—A1 is at the $10^{th}$ bone part on the medial side of 2nd metatarsal and B6 is at the $10^{th}$ bone part on the medial side of 5th metacarpal;

vi) large intestine—A12 is at the $12^{th}$ bone part on the medial side of 5th metatarsal and B8 is at the $12^{th}$ bone part on the medial side of 5th metacarpal;

vii) liver—B1 is at the $10^{th}$ bone part on the medial side of 1st metacarpal;

viii) lungs—B5 is at the $6^{th}$ bone part on the medial side of 5th metacarpal;

ix) ovary—A10 is at the $10^{th}$ bone part on the medial side of 5th metatarsal;

x) pancreas—A5 is at the $9^{th}$ bone part on the lateral side of 2nd metatarsal;

xi) prostata—A6 is at the $10^{th}$ bone part on the lateral side of 2nd metatarsal and A11 is at the $11^{th}$ bone part on the medial side of 5th metatarsal and B4 is at the $11^{th}$ bone part on the lateral side of 4th metacarpal;

xii) rectum—A13 is at the $14^{th}$ bone part on the medial side of 5th metatarsal and B9 is at the $14^{th}$ bone part on the medial side of 5th metacarpal;

xiii) small intestine—A8 is at the $8^{th}$ bone part on the medial side of 5th metatarsal;

xiv) stomach—A4 is at the $8^{th}$ bone part on the lateral side of 2nd metatarsal;

xv) testis—B2 is at the $11^{th}$ bone part on the medial side of 1st metacarpal;

xvi) thyroid—A7 is at the $4^{th}$ bone part on the medial side of 5th metatarsal; and xvii) uterus—A6 is at the $10^{th}$ bone part on the lateral side of 2nd metatarsal and A9 is at the $10^{th}$ bone part on the medial side of 5th metatarsal and B4 is at the $11^{th}$ bone part on the lateral side of 4th metacarpal.

2. The method of claim 1, wherein:

i) providing an instruction material in step (a) and an individual consults the instructional material and decides which of the specific acupoints should be stimulated and prepares a therapy protocol accordingly, without the assistance of a veterinarian or an accredited acupuncture practitioner;

ii) in step (b) the treatment sessions are carried out by the owner of said dog or said cat or by another layperson;

iii) in step (d) an individual, who can be the same or different from the individual of step i), adjusts the treatment protocol with or without the help of a veterinarian or an accredited acupuncture practitioner.

3. The method of claim 1, wherein the at least one stimulation means is selected from the group including, but not limited to: traditional acupuncture needles, auto-injector needles, electric acupuncture apparatus, acupressure devices, lasers, UV radiation sources, infra-red radiation sources, heat sources, magnets, fire, and a combination of at least two of these means.

4. The method of claim 1, wherein the treatment sessions are initially carried out once a week for at least 3 months.

5. The method of claim 1, wherein each treatment session comprises one of the following: using low-level laser radiation alone for 5 minutes for each relevant acupoint; using acupuncture needles alone for 10 minutes per acupoint; and using a combined treatment with acupuncture needles and low-level laser radiation comprised of using said acupuncture needles alone for 5 minutes followed by use of said low-level laser and said acupuncture needles together for an additional 5 minutes.

6. The method of claim 1, wherein the corresponding points on both front paws or on both rear paws are stimulated either simultaneously or consecutively.

7. The method of claim 1, wherein treatment sessions are carried out periodically for the remainder of the animal's life.

8. The method of claim 1 wherein the treatment session is carried out with the aid of at least one of:

a. personalized gloves that comprise holes directly over the specific acupoints that should be stimulated for the specific type of neoplastic process; and b. an apparatus that is adapted to position and to support the stimulation means above the specific acupoint that should be stimulated for the specific type of neoplastic process at the correct location and angle.

9. A method for preventing the occurrence of a specific type of neoplastic process in an organ of any given dog or cat, including a dog or cat having a family history or genetic makeup that increases its risk of contracting said specific type of neoplastic process, said preventive method comprising periodically carrying out a preventive treatment session comprised of stimulation of the specific acupuncture points A1 to A13 and B1 to B9 that are relative to said specific type of neoplastic process;

wherein, each said acupoint location is identified by a number ranging from 1 to 20 that corresponds with a location along a specific bone, each specific bone is divided into twenty parts starting from the distal bone end being the $1^{st}$ bone part and the proximal bone end being the $20^{th}$ bone part and wherein the specific acupoints that are associated with neoplastic process effecting the following organs are:

i) anus—A13 is at the $14^{th}$ bone part on the medial side of 5th metatarsal and B9 is at the $14^{th}$ bone part on the medial side of 5th metacarpal;

ii) bladder—A2 is at the $11^{th}$ bone part on the medial side of 2nd metatarsal and B7 is at the $11^{th}$ bone part on the medial side of 5th metacarpal;

iii) breast—A3 is at the $6^{th}$ bone part on the lateral side of 2nd metatarsal;

iv) cervix—B3 is between the distal ⅔ and the proximal ⅓ on the lateral side of the proximal digital bone of the 4th digit;
v) kidney—A1 is at the $10^{th}$ bone part on the medial side of 2nd metatarsal and B6 is at the $10^{th}$ bone part on the medial side of 5th metacarpal;
vi) large intestine—A12 is at the $12^{th}$ bone part on the medial side of 5th metatarsal and B8 is at the $12^{th}$ bone part on the medial side of 5th metacarpal;
vii) liver—B1 is at the $10^{th}$ bone part on the medial side of 1st metacarpal;
viii) lungs—B5 is at the $6^{th}$ bone part on the medial side of 5th metacarpal;
ix) ovary—A10 is at the $10^{th}$ bone part on the medial side of 5th metatarsal;
x) pancreas—A5 is at the $9^{th}$ bone part on the lateral side of 2nd metatarsal;
xi) prostata—A6 is at the $10^{th}$ bone part on the lateral side of 2nd metatarsal and A11 is at the $11^{th}$ bone part on the medial side of 5th metatarsal and B4 is at the $11^{th}$ bone part on the lateral side of 4th metacarpal;
xii) rectum—A13 is at the $14^{th}$ bone part on the medial side of 5th metatarsal and B9 is at the $14^{th}$ bone part on the medial side of 5th metacarpal;
xiii) small intestine—A8 is at the $8^{th}$ bone part on the medial side of 5th metatarsal;
xiv) stomach—A4 is at the $8^{th}$ bone part on the lateral side of 2nd metatarsal;
xv) testis—B2 is at the $11^{th}$ bone part on the medial side of 1st metacarpal;
xvi) thyroid—A7 is at the $4^{th}$ bone part on the medial side of 5th metatarsal; and
xvii) uterus—A6 is at the $10^{th}$ bone part on the lateral side of 2nd metatarsal and A9 is at the $10^{th}$ bone part on the medial side of 5th metatarsal and B4 is at the $11^{th}$ bone part on the lateral side of 4th metacarpal.

10. The method of claim 9, wherein each preventive treatment session comprises one of the following: using low-level laser radiation alone for 5 minutes for each relevant acupoint; using acupuncture needles alone for 10 minutes per acupoint; and using a combined treatment with acupuncture needles and low-level laser radiation comprised of using said acupuncture needles alone for 5 minutes followed by use of said low-level laser and said acupuncture needles together for an additional 5 minutes.

11. The method of claim 9, wherein the preventive treatment sessions are carried out once every three months.

12. The method of claim 9 wherein the preventive treatment session is carried out with the aid of at least one of:
a) personalized gloves that comprise holes directly over the specific acupoints that should be stimulated for the specific type of neoplastic process; and
b) an apparatus that is adapted to position and to support the stimulation means above the specific acupoint that should be stimulated for the specific type of neoplastic process at the correct location and angle.

* * * * *